(12) United States Patent
Fortescue et al.

(10) Patent No.: US 9,772,339 B2
(45) Date of Patent: Sep. 26, 2017

(54) METHODS AND SYSTEMS FOR IMAGE ANALYSIS IDENTIFICATION

(71) Applicant: LIFE TECHNOLOGIES CORPORATION, Carlsbad, CA (US)

(72) Inventors: David Fortescue, San Francisco, CA (US); Ming Shen, Singapore (SG); Woon Liang Soh, Singapore (SG); Francis T. Cheng, Palo Alto, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/348,031

(22) PCT Filed: Sep. 28, 2012

(86) PCT No.: PCT/US2012/057714
§ 371 (c)(1),
(2) Date: Mar. 27, 2014

(87) PCT Pub. No.: WO2013/049442
PCT Pub. Date: Apr. 4, 2013

(65) Prior Publication Data
US 2014/0247967 A1    Sep. 4, 2014

Related U.S. Application Data

(60) Provisional application No. 61/541,453, filed on Sep. 30, 2011.

(51) Int. Cl.
*G06K 7/00* (2006.01)
*G01N 35/00* (2006.01)
(Continued)

(52) U.S. Cl.
CPC ..... *G01N 35/00732* (2013.01); *G06T 7/0012* (2013.01); *G01N 35/028* (2013.01);
(Continued)

(58) Field of Classification Search
CPC .......... G01N 35/00732; G01N 35/028; G01N 2035/00752; G06T 7/0012; G06T 2207/10004; G06T 2207/30004
(Continued)

(56) References Cited

U.S. PATENT DOCUMENTS

| | | | |
|---|---|---|---|
| 6,558,623 B1 | 5/2003 | Ganz et al. | |
| 2003/0059964 A1* | 3/2003 | Kawai | G05B 19/4183 438/14 |

(Continued)

FOREIGN PATENT DOCUMENTS

| | | |
|---|---|---|
| CN | 1886663 A | 12/2006 |
| JP | 8-96059 A | 4/1996 |
| JP | 2010-524001 A | 7/2010 |

OTHER PUBLICATIONS

International Search Report with Written Opinion for International Application No. PCT/US2012/057714 dated Dec. 18, 2012.

*Primary Examiner* — Amandeep Saini
(74) *Attorney, Agent, or Firm* — Mauriel Kapouytian Woods LLP; Lana Akopyan; Michael Mauriel

(57) ABSTRACT

A computer-implemented method for identifying a first object-of-interest is provided. The first object-of-interest includes two identifiers and a sample portion. The method includes imaging the first object-of-interest including the two identifiers. The imaging generates a first set of image data. The method further includes determining a position of the first object-of-interest in the field-of-view of an optical sensor and determining the two identifiers from the first set of image data. The method includes identifying the first object-of-interest based on the two identifiers.

16 Claims, 10 Drawing Sheets

(51) Int. Cl.
*G06T 7/00* (2017.01)
*G01N 35/02* (2006.01)
*G01N 15/00* (2006.01)

(52) U.S. Cl.
CPC .............. *G01N 2015/0053* (2013.01); *G01N 2035/00752* (2013.01); *G06T 2207/10004* (2013.01); *G06T 2207/30004* (2013.01)

(58) Field of Classification Search
USPC ........................................................ 382/103
See application file for complete search history.

(56) References Cited

U.S. PATENT DOCUMENTS

| | | | |
|---|---|---|---|
| 2004/0239916 A1* | 12/2004 | Seino | G01N 15/1475 356/28.5 |
| 2005/0146719 A1* | 7/2005 | Chhibber | G01J 3/10 356/370 |
| 2006/0088928 A1 | 4/2006 | Sweet et al. | |
| 2006/0216696 A1* | 9/2006 | Goguen | G01N 33/54326 435/5 |
| 2007/0111301 A1 | 5/2007 | Fujita et al. | |
| 2008/0254544 A1 | 10/2008 | Modzelewski et al. | |
| 2009/0214088 A1 | 8/2009 | Sorenson et al. | |
| 2010/0045789 A1 | 2/2010 | Fleming et al. | |

* cited by examiner

METHODS AND SYSTEMS FOR IMAGE ANALYSIS IDENTIFICATION

CROSS-REFERENCE TO RELATED APPLICATIONS

This application claims the benefit of priority of U.S. provisional application Ser. No. 61/541,453, filed Sep. 30, 2011, which is incorporated herein by reference in its entirety.

BACKGROUND

Generally, there is an increasing need to automate systems to increase efficiency. For example, advances in automated biological sample processing instruments allow for quicker, more efficient, and high throughput analysis of samples. These types of systems may assay a greater number of samples than previous systems. As such, samples undergoing various assays are labeled or marked with identifiers.

Previously, an operator of the system or instrument may have had to manually track and validate samples by reading the identifiers on sample containers, racks, or assay chips. This type of manual tracking and validation can be labor-intensive and include a high probability of operator error such as sample mistracking, or improper testing. Furthermore, the greater number of samples desired to be assayed would be more time intensive and cumbersome.

Other more automated systems may scan for identifiers to track and validate samples before testing. However, these systems often need additional components. Furthermore, the identifiers may be misread or unreadable by the systems.

SUMMARY

In one exemplary embodiment, a computer-implemented method for identifying a first object-of-interest is provided. The first object-of-interest includes two identifiers and a sample portion. The method includes imaging the first object-of-interest including the two identifiers. The imaging generates a first set of image data. The method further includes determining a position of the first object-of-interest in the field-of-view of an optical sensor and determining the two identifiers from the first set of image data. The method includes identifying the first object-of-interest based on the two identifiers.

DETAILED DESCRIPTION

Figure 1:
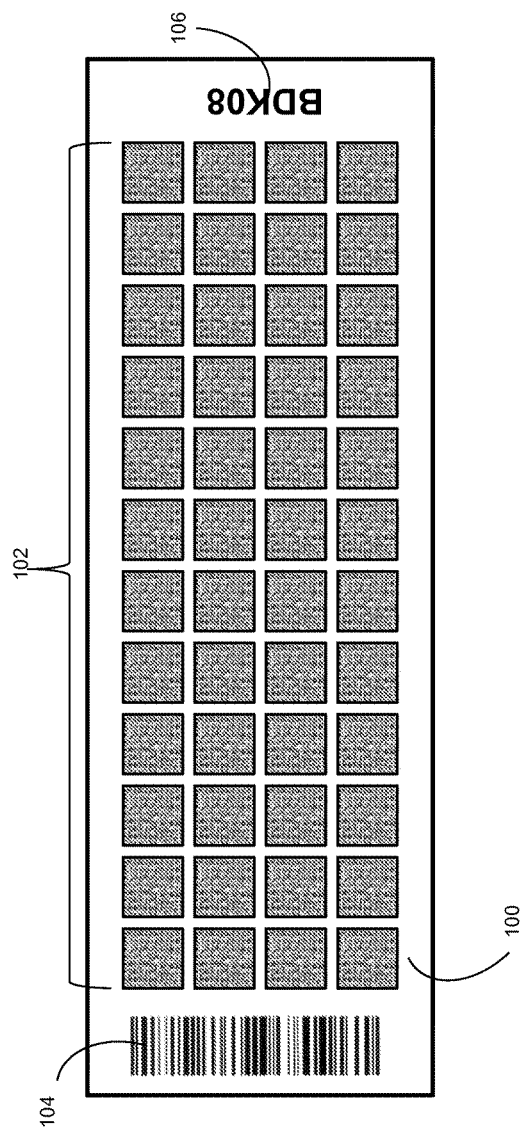
FIG. 1 illustrates an exemplary object-of-interest according to various embodiments described herein.

Exemplary systems for methods related to the various embodiments described in this document include those described in U.S. Provisional Patent Application No. 61/541,453, U.S. Provisional Patent Application No. 61/541,515, U.S. Provisional Patent Application No. 61/541,342, U.S. Provisional Patent Application No. 29/403,049, U.S. Provisional Patent Application No. 61/541,495, U.S. Provisional Patent Application No. 61/541,366, and U.S. Provisional Patent Application No. 61/541,371, all of which are filed Sep. 30, 2011, and all of which are also incorporated herein in their entirety by reference. Exemplary systems for methods related to the various embodiments described in this document include those described in U.S. Provisional Patent Application No. 61/660,343, filed Jun. 15, 2012, which is also incorporated herein in its entirety by reference.

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

As described above, as the number of items a system needs to process are increased, a more automated system is desired. Furthermore, more accurate and efficient identification, tracking, validation, security, and checking for compatibility, for example, are also desired. As such, samples and assays are often labeled with machine-readable identifiers. Examples of identifiers could be alphanumeric characters or a barcode.

The present application relates to reading identifiers on an object-of-interest and, more particularly, to identifying an object by analyzing an image of identifiers on the object-of-interest.

A barcode is a machine-readable representation of data about the object it labels, usually in the form of varying widths and spacing of parallel lines. One type of barcode, barcode 128 encodes character ASCII and symbols using bars and spaces. The encoding is based on the width of each bar and space. Each bar or space has a width that varies between one and four units. Every character is encoded in three bars and three spaces, and the width totals in 11 units.

It should be recognized that the methods and systems described herein may be implemented in various types of systems, instruments, and machines. For example, various embodiments may be implemented in an instrument that performs polymerase chain reactions (PCR) on a plurality of samples.

According to embodiments described herein, a substrate including one or a plurality of samples within one or a plurality of reaction sites may be marked with more than one identifier. Having at least two identifiers to read provides more confirmation that the identifier reading is accurate. In some cases, an identifier may not be able to be detected by the system. In other cases, an identifier may be inaccurately read and identify an incorrect sample or assay. By having more than one identifier, an extra check can be made to identify the sample.

In various embodiments, the devices, instruments, systems, and methods described herein may be used to detect one or more types of biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. Embodiments of the present disclosure are generally directed to devices, instruments, systems, and methods for monitoring or measuring a biological reaction for a large number of small volume samples. As used herein, samples may be referred to as sample volumes, or reactions volumes, for example.

While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, qPCR, genome walking, and bridge PCR, for example.

As described below, in accordance with various embodiments described herein, reaction sites may include, but are not limited to, through-holes, wells, indentations, spots, cavities, sample retainment regions, and reaction chambers, for example.

Furthermore, as used herein, thermal cycling may include using a thermal cycler, isothermal amplification, thermal convection, infrared mediated thermal cycling, or helicase dependent amplification, for example. In some embodiments, the chip may be integrated with a built-in heating element. In various embodiments, the chip may be integrated with semiconductors.

According to various embodiments, detection of a target may be, but is not limited to, fluorescence detection, detection of positive or negative ions, pH detection, voltage detection, or current detection, alone or in combination, for example.

Various embodiments described herein are particularly suited for digital PCR (dPCR). In digital PCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the sample containing the target nucleotide sequence are amplified and produce a positive detection signal, while the samples containing no target nucleotide sequence are not amplified and produce no detection signal. Using Poisson statistics, the number of target nucleotide sequences in the original solution may be correlated to the number of samples producing a positive detection signal. Positive and negative detection can be determined or validated by amplification quality metrics according to various embodiments of the present teachings.

Substrate

In various embodiments, a substrate may have a plurality of sample regions, or reaction sites, configured for receiving a plurality of samples, wherein the reaction sites may be sealed within the substrate via a lid between the reaction sites and heated cover 210. Some examples of a sample holder may include, but are not limited to, a multi-well plate, such as a standard microtiter 96-well plate, a 384-well plate, a microcard, a through-hole array, or a substantially planar holder, such as a glass or plastic slide. The reaction sites in various embodiments of a sample holder may include depressions, indentations, ridges, and combinations thereof, patterned in regular or irregular arrays formed on the surface of the sample holder substrate.

According to various embodiments of the present teachings, each reaction sites may have a volume of about 1.3 nanoliters. Alternatively, the volume each reaction site may be less than 1.3 nanoliters. This may be achieved, for example, by decreasing the diameter of reaction site 104 and/or the thickness of the sample holder. For example, each reaction site 104 may have a volume that is less than or equal to 1 nanoliter, less than or equal to 100 picoliters, less than or equal to 30 picoliters, or less than or equal to 10 picoliters. In other embodiments, the volume some or all of the reaction sites 104 is in a range of 1 to 20 nanoliters.

In some embodiments, the reaction sites are through-holes. In these examples, each through-hole has a volume of about 1.3 nanoliters. Alternatively, the volume each through-hole may be less than 1.3 nanoliters. This may be achieved, for example, by decreasing the diameter of through-hole and/or the thickness of the sample holder substrate. For example, each through-hole may have a volume that is less than or equal to 1 nanoliter, less than or equal to 100 picoliters, less than or equal to 30 picoliters, or less than or equal to 10 picoliters. In other embodiments, the volume some or all of the through-holes is in a range of 1 to 20 nanoliters.

In various embodiments, a density of reaction sites 104 may be at least 100 reaction sites per square millimeter. In other embodiments, there may be higher densities of reaction sites. For example, a density of reaction sites 104 within chip 100 may be greater than or equal to 150 reaction sites per square millimeter, greater than or equal to 200 reaction sites per square millimeter, greater than or equal to 500 reaction sites per square millimeter, greater than or equal to 1,000 reaction sites per square millimeter, greater than or equal to 10,000 reaction sites per square millimeter.

In some embodiments, the reaction sites are through-holes. Accordingly, a density of through-holes within a sample holder substrate may be greater than or equal to 150 through-holes per square millimeter, greater than or equal to 200 through-holes per square millimeter, greater than or equal to 500 through-holes per square millimeter, greater than or equal to 1,000 through-holes per square millimeter, greater than or equal to 10,000 through-holes per square millimeter.

FIG. 1 illustrates a substrate 100 labeled with two identifiers according to various embodiments. A plurality of samples may be included in the reaction site area 102 for testing on a single substrate 100. The reaction site area 102 is illustrated as an array. In other examples, a reaction site area may include one sample. In some embodiments, a plurality of substrates 100 may be in a system for testing. For example, two, four, or twenty substrates 100 may be put in an instrument system for testing. The assay components may also be preloaded along with the sample in the reaction sites in some embodiments.

The machine-readable identifiers in the embodiment shown in FIG. 1 are a barcode 104 and an alphanumeric code 106. However, it should be recognized that the machine-readable identifiers, according to embodiments described in this document, may be barcodes, text, numerals, QR codes, or other symbols, for example, and any combination thereof. It should also be noted that an alphanumeric identifier is also human-readable and can be validated against a machine-read result.

Computer-Implemented System

Methods of detection and processing of identifiers in accordance with embodiments described herein, may be implemented in a computer system.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

Figure 2:
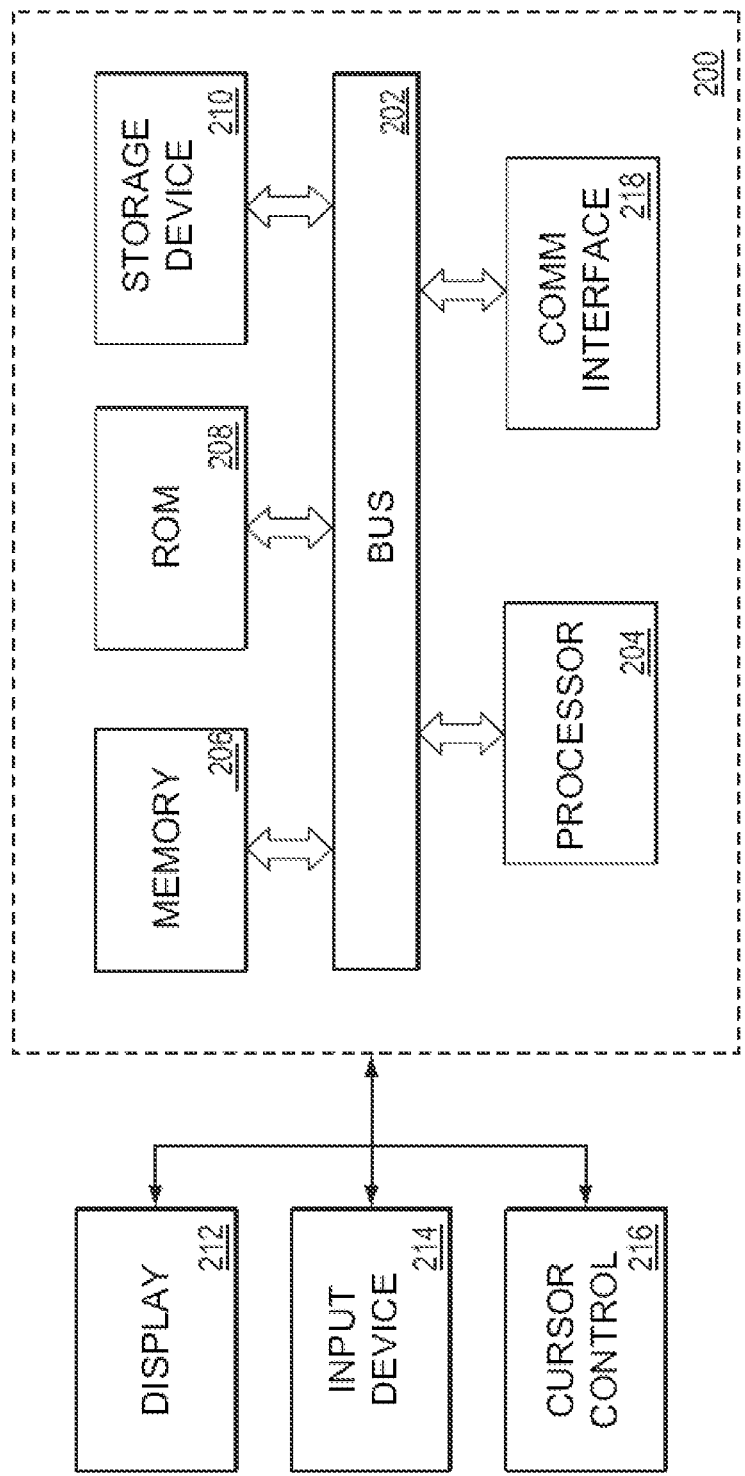
FIG. 2 is a block diagram that illustrates a computer system, upon which embodiments of the present teachings may be implemented.

FIG. 2 is a block diagram that illustrates a computer system 200 that may be employed to carry out processing functionality, according to various embodiments. Instruments to perform experiments may be connected to the exemplary computing system 200. According to various embodiments, the instruments that may be utilized are a thermal cycler system 200 of FIG. 2 or a thermal cycler system 300 of FIG. 3 may utilize. Computing system 200 can include one or more processors, such as a processor 204. Processor 204 can be implemented using a general or special purpose processing engine such as, for example, a microprocessor, controller or other control logic. In this example, processor 204 is connected to a bus 202 or other communication medium.

Further, it should be appreciated that a computing system 200 of FIG. 2 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 200 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 200 may be configured to connect to one or more servers in a distributed network. Computing system 200 may receive information or updates from the distributed network. Computing system 200 may also transmit information to be stored within the distributed network that may be accessed by other clients connected to the distributed network.

Computing system 200 may include bus 202 or other communication mechanism for communicating information, and processor 204 coupled with bus 202 for processing information.

Computing system 200 also includes a memory 206, which can be a random access memory (RAM) or other dynamic memory, coupled to bus 202 for storing instructions to be executed by processor 204. Memory 206 also may be used for storing temporary variables or other intermediate information during execution of instructions to be executed by processor 204. Computing system 200 further includes a read only memory (ROM) 208 or other static storage device coupled to bus 202 for storing static information and instructions for processor 204.

Computing system 200 may also include a storage device 210, such as a magnetic disk, optical disk, or solid state drive (SSD) is provided and coupled to bus 202 for storing information and instructions. Storage device 210 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 210 may include other similar instrumentalities for allowing computer programs or other instructions or data to be loaded into computing system 200. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 210 to computing system 200.

Computing system 200 can also include a communications interface 218. Communications interface 218 can be used to allow software and data to be transferred between computing system 200 and external devices. Examples of communications interface 218 can include a modem, a network interface (such as an Ethernet or other NIC card), a communications port (such as for example, a USB port, a RS-232C serial port), a PCMCIA slot and card, Bluetooth, etc. Software and data transferred via communications interface 218 are in the form of signals which can be electronic, electromagnetic, optical or other signals capable of being received by communications interface 218. These signals may be transmitted and received by communications interface 218 via a channel such as a wireless medium, wire or cable, fiber optics, or other communications medium. Some examples of a channel include a phone line, a cellular phone link, an RF link, a network interface, a local or wide area network, and other communications channels.

Computing system 200 may be coupled via bus 202 to a display 212, such as a cathode ray tube (CRT) or liquid crystal display (LCD), for displaying information to a computer user. An input device 214, including alphanumeric and other keys, is coupled to bus 202 for communicating information and command selections to processor 204, for example. An input device may also be a display, such as an LCD display, configured with touchscreen input capabilities.

Another type of user input device is cursor control 216, such as a mouse, a trackball or cursor direction keys for communicating direction information and command selections to processor 204 and for controlling cursor movement on display 212. This input device typically has two degrees of freedom in two axes, a first axis (e.g., x) and a second axis (e.g., y), that allows the device to specify positions in a plane. A computing system 200 provides data processing and provides a level of confidence for such data. Consistent with certain implementations of embodiments of the present teachings, data processing and confidence values are provided by computing system 200 in response to processor 204 executing one or more sequences of one or more instructions contained in memory 206. Such instructions may be read into memory 206 from another computer-readable medium, such as storage device 210. Execution of the sequences of instructions contained in memory 206 causes processor 204 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 204 for execution. Such instructions, generally referred to as "computer program code" (which may be grouped in the form of computer programs or other groupings), when executed, enable the computing system 200 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 210. Volatile media includes dynamic memory, such as memory 206. Transmission media includes coaxial cables, copper wire, and fiber optics, including the wires that comprise bus 202.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 204 for execution. For example, the instructions may initially be carried on magnetic disk of a remote computer. The remote computer can load the instructions into its dynamic memory and send the instructions over a telephone line using a modem. A modem local to computing system 200 can receive the data on the telephone line and use an infra-red transmitter to convert the data to an infra-red signal. An infra-red detector coupled to bus 202 can receive the data carried in the infra-red signal and place the data on bus 202. Bus 202 carries the data to memory 206, from which processor 204 retrieves and executes the instructions. The instructions received by memory 206 may optionally be stored on storage device 210 either before or after execution by processor 204.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

PCR Instruments

Figure 3:
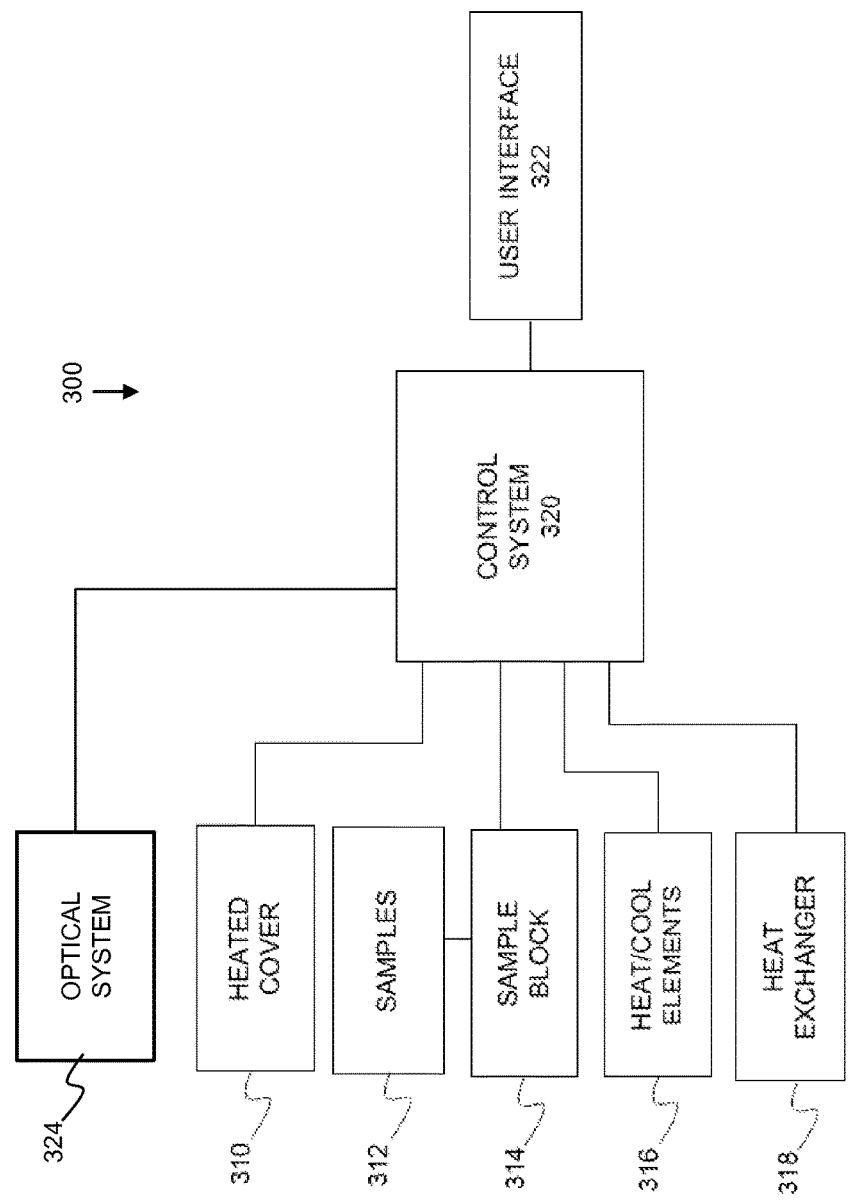
FIG. 3 is a block diagram that illustrates an exemplary instrument, upon which embodiments of the present teachings may be implemented.

As mentioned above, an instrument that may be utilized according to various embodiments, but is not limited to, is a polymerase chain reaction (PCR) instrument. FIG. 3 is a block diagram that illustrates a PCR instrument 300, upon which embodiments of the present teachings may be implemented. PCR instrument 300 may include a heated cover 310 that is placed over a plurality of samples 312 contained in a substrate (not shown). In various embodiments, a substrate may be a glass or plastic slide with a plurality of sample regions, which sample regions have a cover between the sample regions and heated cover 310. Some examples of a substrate may include, but are not limited to, a multi-well plate, such as a standard microtiter 96-well, a 384-well plate, or a microcard, or a substantially planar support, such as a glass or plastic slide. The reaction sites in various embodiments of a substrate may include depressions, indentations, ridges, and combinations thereof, patterned in regular or irregular arrays formed on the surface of the substrate. Various embodiments of PCR instruments include a sample block 314, elements for heating and cooling 316, a heat exchanger 318, control system 320, and user interface 322. Various embodiments of a thermal block assembly according to the present teachings comprise components 314-318 of PCR instrument 300 of FIG. 3.

Real-time PCR instrument 300 has an optical system 324. In FIG. 3, an optical system 324 may have an illumination source (not shown) that emits electromagnetic energy, an optical sensor, detector, or imager (not shown), for receiving electromagnetic energy from samples 312 in a substrate, and optics 340 used to guide the electromagnetic energy from each DNA sample to the imager. For embodiments of PCR instrument 300 in FIG. 3 and real-time PCR instrument 300 in FIG. 3, control system 320, may be used to control the functions of the detection system, heated cover, and thermal block assembly. Control system 320 may be accessible to an end user through user interface 322 of PCR instrument 300 in FIG. 3 and real-time PCR instrument 300 in FIG. 3. Also a computer system 200, as depicted in FIG. 2, may serve as to provide the control the function of PCR instrument 300 in FIG. 3, as well as the user interface function. Additionally, computer system 200 of FIG. 2 may provide data processing, display and report preparation functions. All such instrument control functions may be dedicated locally to the PCR instrument, or computer system 200 of FIG. 2 may provide remote control of part or all of the control, analysis, and reporting functions, as will be discussed in more detail subsequently.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Optical System for Imaging

Figure 4:
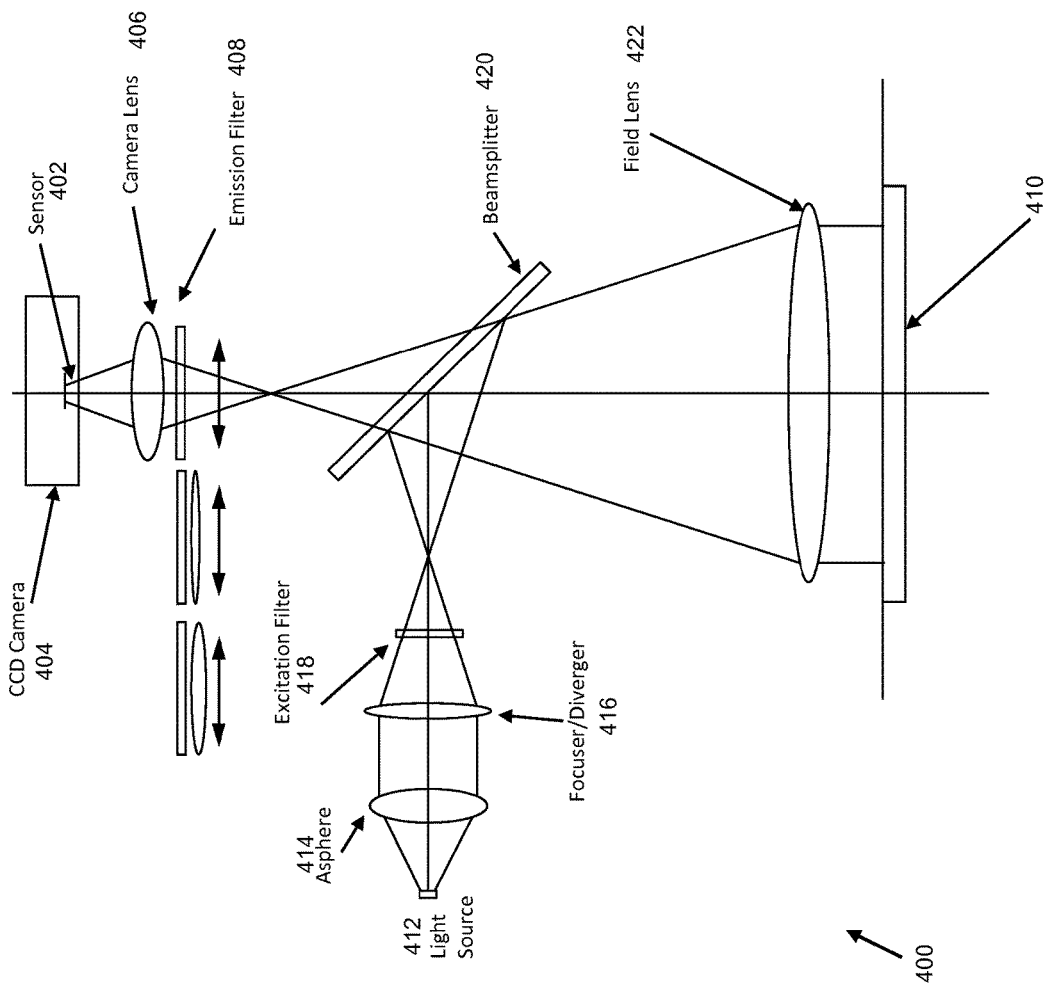
FIG. 4 illustrates an exemplary optical system for imaging according to various embodiments described herein.

FIG. 4 depicts an exemplary optical system 400 that may be used for imaging according to embodiments described herein. It should be recognized that optical system 400 is an exemplary optical system and one skilled in the art would recognize that other optical systems may be used to image an object-of-interest. According to various embodiments, an object of interest may be a substrate as described herein. An optical sensor 402 included in a camera 404, for example, may image an object-of-interest 410. Object-of-interest may be an array chip, a plurality of array chips, or a substrate including the sample for assaying, for example. The optical sensor 402 may be a CCD sensor and the camera 404 may be a CCD camera. Further, the optical sensor includes a camera lens 406.

Depending on the object of interest, an emission filter 408 is chosen for imagining the object-of-interest 410 according to various embodiments. Emission filter 408 may be changed to image fluorescent emission emitted from the object-of-interest 401 in other embodiments.

Optical system 400 may use a reflected light source 412 to image object-of-interest 410. The light from light source 412 may be filtered through an asphere 414, a focuser/diverger 416, and excitation filter 418 before being reflected to the object-of-interest 410 by beamsplitter 420. Optical system 400 may also include a field lens 422.

Image

Figure 5:
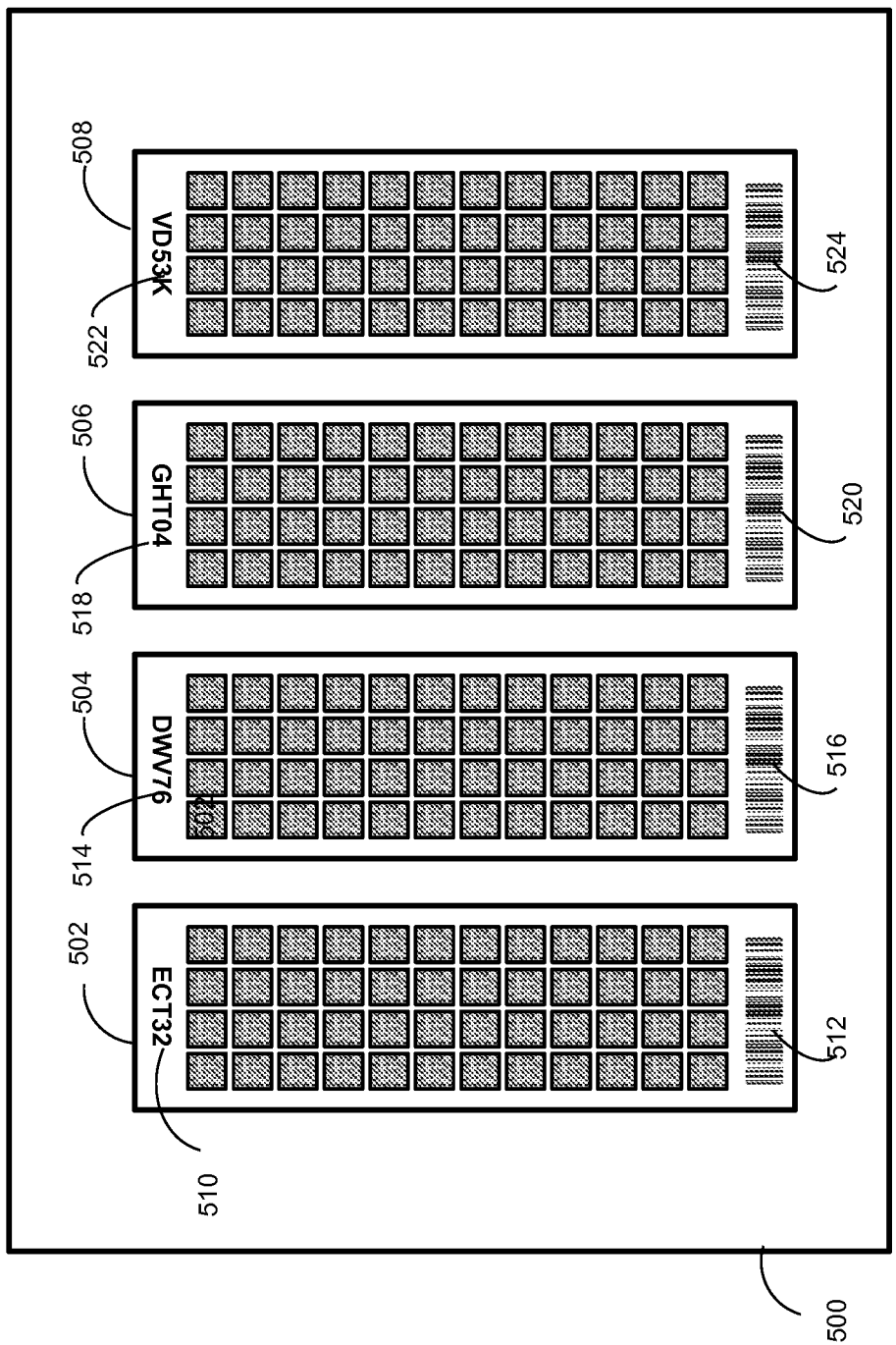
FIG. 5 illustrates an image of objects-of-interest and associated identifiers according to various embodiments described herein.

As described above, optical system 400 as depicted in FIG. 4, may image an object-of-interest. The object-of-interest may be a substrate. A substrate may be a consumable, such as an array chip (as depicted in FIG. 1). The object-of-interest may also be a plurality of substrates, as depicted in FIG. 5. In exemplary image 500 depicted in FIG. 5, four substrates 502, 504, 506, and 508 are included in image 500. It should be recognized that an image may include one or more objects according to various embodiments described herein. Each substrate includes two identifiers. For example, substrate 502 is marked with identifier 510 and identifier 512. As mentioned above, identifiers may be a symbol, an alphanumeric code, or a barcode, for example. In image 500, substrate 502 has an identifier 510 as an alphanumeric code and identifier 512 as a barcode. In accordance with other embodiments, an object that is imaged may include identifiers that are any combination of symbols, alphanumeric codes, or bar codes, for example.

After an optical sensor 402 (FIG. 4) images at least one object including an identifier, such as a barcode, the image is analyzed to read the identifiers. For example, a barcode identifier is read using the image in contrast to a scanning method.

The identifiers may be used to identifier the assays included on the substrate, or object. The assay type associated with the identifier may be stored in a database, or memory, such as memory 206 (FIG. 2). If an object is labeled with two identifiers, each identifier may be independently determined according to embodiments described herein. In this case, each identifier determination may be validated by determining if the other identifier is associated. Identifier associations may be stored in memory 206 (FIG. 2) of computer system 200. In other embodiments, after determining the identifiers and associated assay types of the plurality of substrates in the image, compatibility of assay types of being tested in the same run may be determined.

For example, if substrates 502, 504, 506, and 508 (FIG. 5) were to be tested in the PCR instrument 300 (FIG. 3), after identifying substrates 502, 504, 506, and 508 from the image 500 (FIG. 5), processor 204 (FIG. 2) may determine if the assay types associated with substrates 502, 504, 506, and 508 are compatible.

Furthermore, if any identifier in image 500 cannot be read, this may indicate an substrate is not in the correct position. The system may then indicate incorrect positioning or an incorrect substrate to the user if the system cannot identify an substrate, such as displaying an indication on a user interface 322 (FIG. 3).

Figure 6:
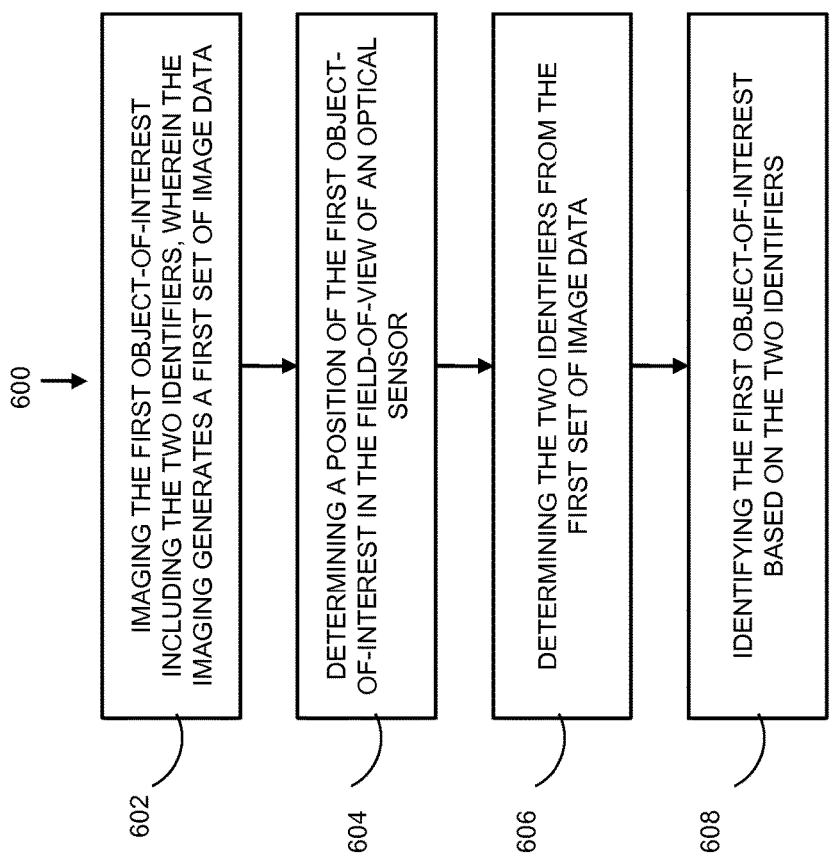
FIG. 6 illustrates a flowchart of a method for identifying objects by image analysis according to various embodiments described herein.

FIG. 6 illustrates a flowchart depicting an exemplary method 600 of identifying an object-of-interest according to embodiments described herein. The steps of method 600 may be implemented by a processor 204, as shown in FIG. 2. Furthermore, instructions for executing the method by processor 204 may be stored in memory 206.

With reference to FIG. 6, in step 602, the object-of-interest may be imaged. The object-of-interest includes two identifiers. The two identifiers are imaged along with the object-of-interest. The object-of-interest may be imaged with an optical system 400, as described above. In response to the imaging of the object-of-interest, image data is generated. The image data may be stored in memory 206 (FIG. 2).

Determining a Position of Object-of-Interest within Image

With reference to FIG. 6, in step 604, the object-of-interest may be positioned in the field-of-view of an optical sensor. Further, also mentioned above, the object-of-interest may be an substrate according to embodiments of the teachings described herein. By positioning the object-of-interest adequately, the indicators in an image will be in an expected position on the image. As such, the image may be analyzed in the expected position to read the indicators. The expected position may be within a region-of-interest (ROI).

The expected position of the indicators is further determined by determining a point-of-reference within the image. According to various embodiments, the center of an object-of-interest within the image is determined by image analysis techniques. By knowing a point-of-reference and dimensions of the object-of-interest, expected positions within the image of the identifiers and other landmarks can be searched.

The position of the object-of-interest may be determined by processor 204 (FIG. 2). The sample area 102 (FIG. 1) may be used to determine the ROI. Sample area 102, may include wells or holes, for example. More particularly, since the dimensions of the object-of-interest and the position of the indicators on the object-of-interest are both predetermined, sample area can be used to determine the ROI, in which the indicators may be found in the image. The ROI may be a shape, such as a rectangle, where the indicator is expected to be found within the image. As such, processor 204 may execute instructions to analyze image data to read the indicator.

With reference back to FIG. 6, in step 606, the identifiers marked on the object-of-interest are determined. In other words, the identifiers are read so that the object-of-interest may be identified.

Reading Identifiers

Figure 7:
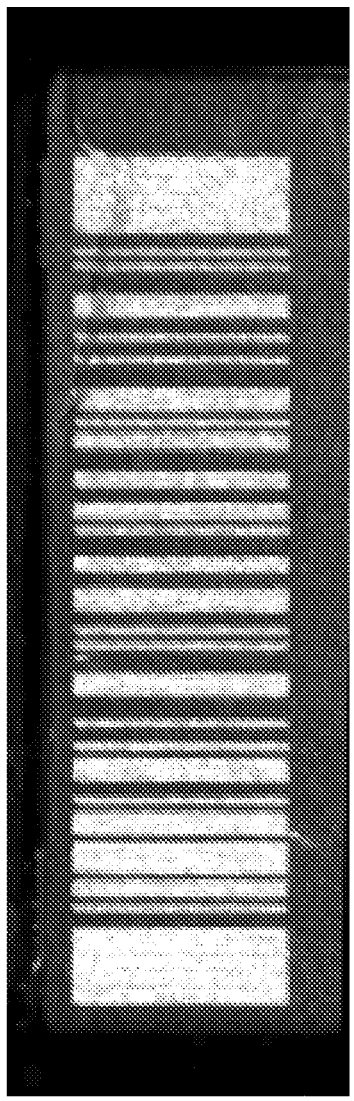
FIG. 7 illustrates an identifier according to various embodiments described herein.

As described above, an indicator may be a barcode. The image data within the ROI is processed, or analyzed, by processor 204. The barcode data is determined from the image data within the ROI. An example of an imaged barcode is shown in FIG. 7. The barcode data may be determined by finding the dark and light zones of the barcode in the image. The image data may be filtered in some embodiments to more clearly define the dark and light zones of the barcode.

The dark and light zones can be determined by sampling and filtering methods known by one skilled in the art. Decisions on whether the image data is a dark or light region can be determined by comparing against a predetermined threshold. In other words, the spaces and bars of the barcode are measured.

The dark and light zones are measured and the barcode can be read. After identifying the barcode from the object-of-interest, the associated data with the barcode can be determined. The identifier data its associated data is stored within memory 206. Associated data may include assay type, or other information such as sample data.

Also described above, an indicator may be an alphanumeric code or other symbol. Stored in a database or memory 206, for example, templates of possible alphanumeric characters or symbols may be stored as binary images.

Figure 8A:
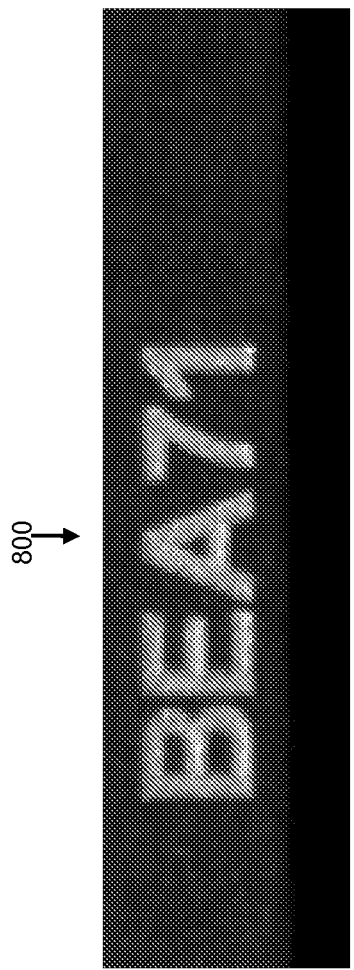
FIG. 8A illustrates another identifier according to various embodiments described herein.
Figure 8B:
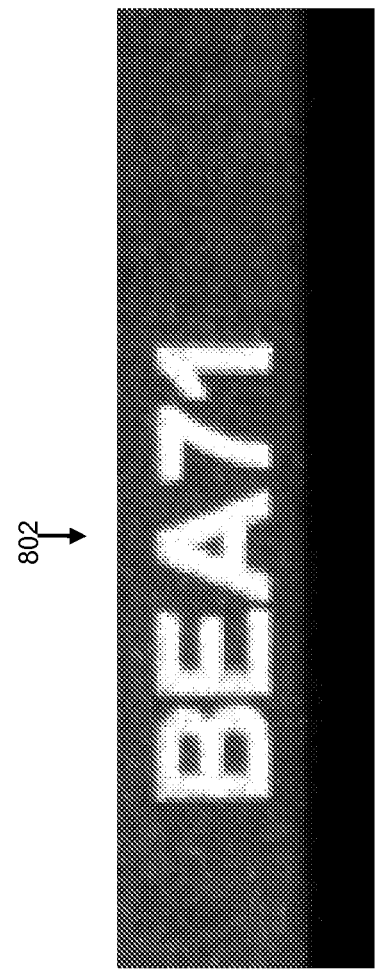
FIG. 8B illustrates the identifier shown in FIG. 8A after preprocessing according to various embodiments described herein.

The image may be preprocessed to create more clearly defined dark and light regions. For example, the gray levels of the image data including an alphanumeric indicator may be determined. When the gray levels are below a certain threshold level, the image data may be determined as a light region. To illustrate the effects of preprocessing, FIG. 8A illustrates an alphanumeric character before preprocessing. FIG. 8B depicts the alphanumeric character after preprocessing.

As described above, an alphanumeric indicator may be included in the ROI. The image data within the ROI is parsed and a binary map of each character can be generated. As such, the determined binary map may be compared to the stored templates of alphanumeric characters. Each character can be determined by finding a match in the stored templates. In this way, the alphanumeric code can be read. If the indicator is a symbol, the symbol may be determined in a similar manner.

After determining results for both indicators, each indicator result may be validated with the other indicator result. In other words, the determined indicator should be associated with the same object-of-interest of the other determined indicator.

Furthermore, as described above, the indicators identify the object-of-interest, or the substrate, as in step 608 (FIG. 6). The assay type may be identified. If other substrates are included in the system for a test, the assay types of each substrate may be compared to check for compatibility. If it is determined that an substrate should not be run with another substrate, an indicator of the error may be displayed to the user on a user interface.

Figure 9A:
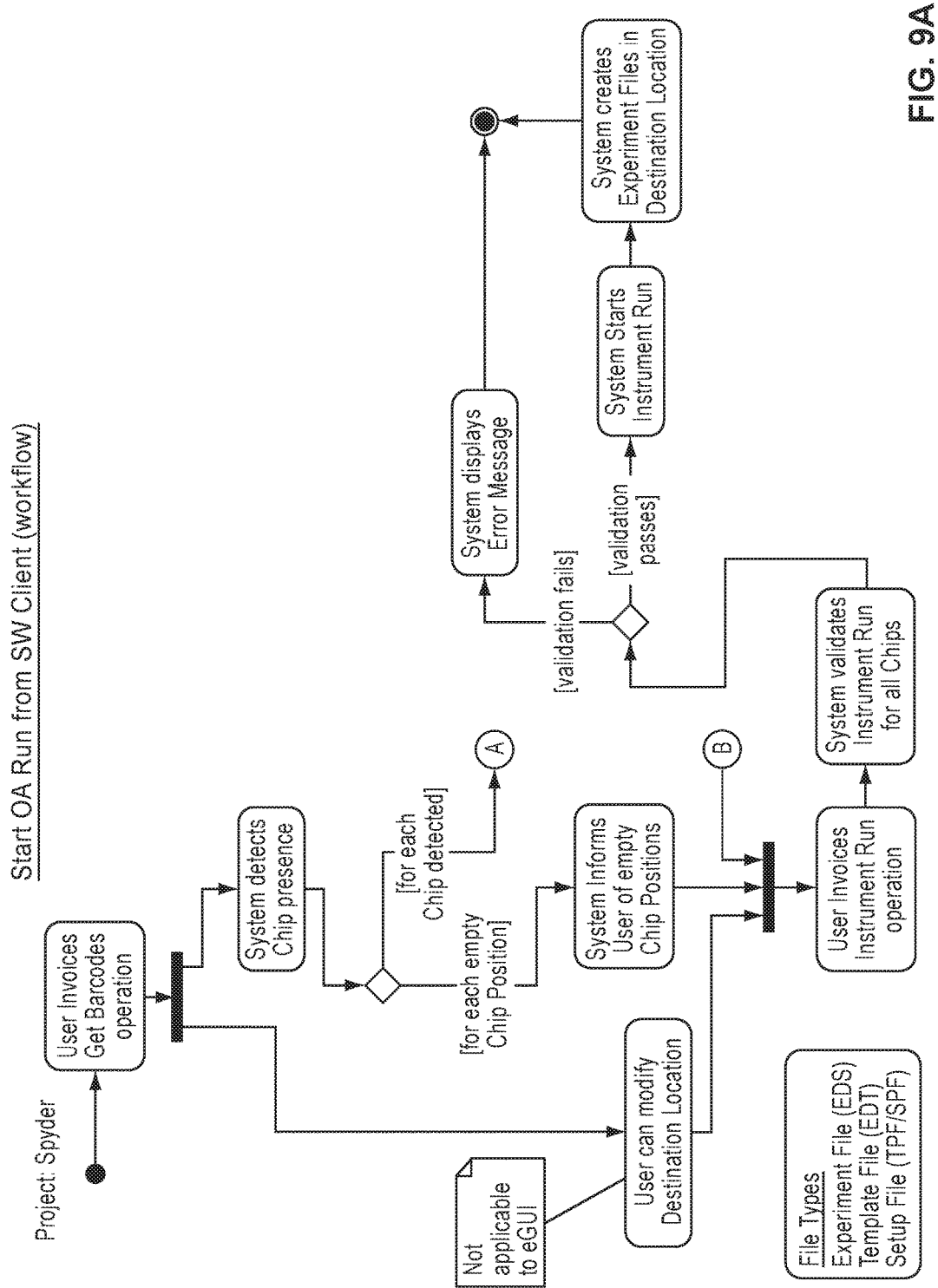
FIGS. 9A and 9B illustrate an exemplary workflow according to embodiments described herein.
Figure 9B:
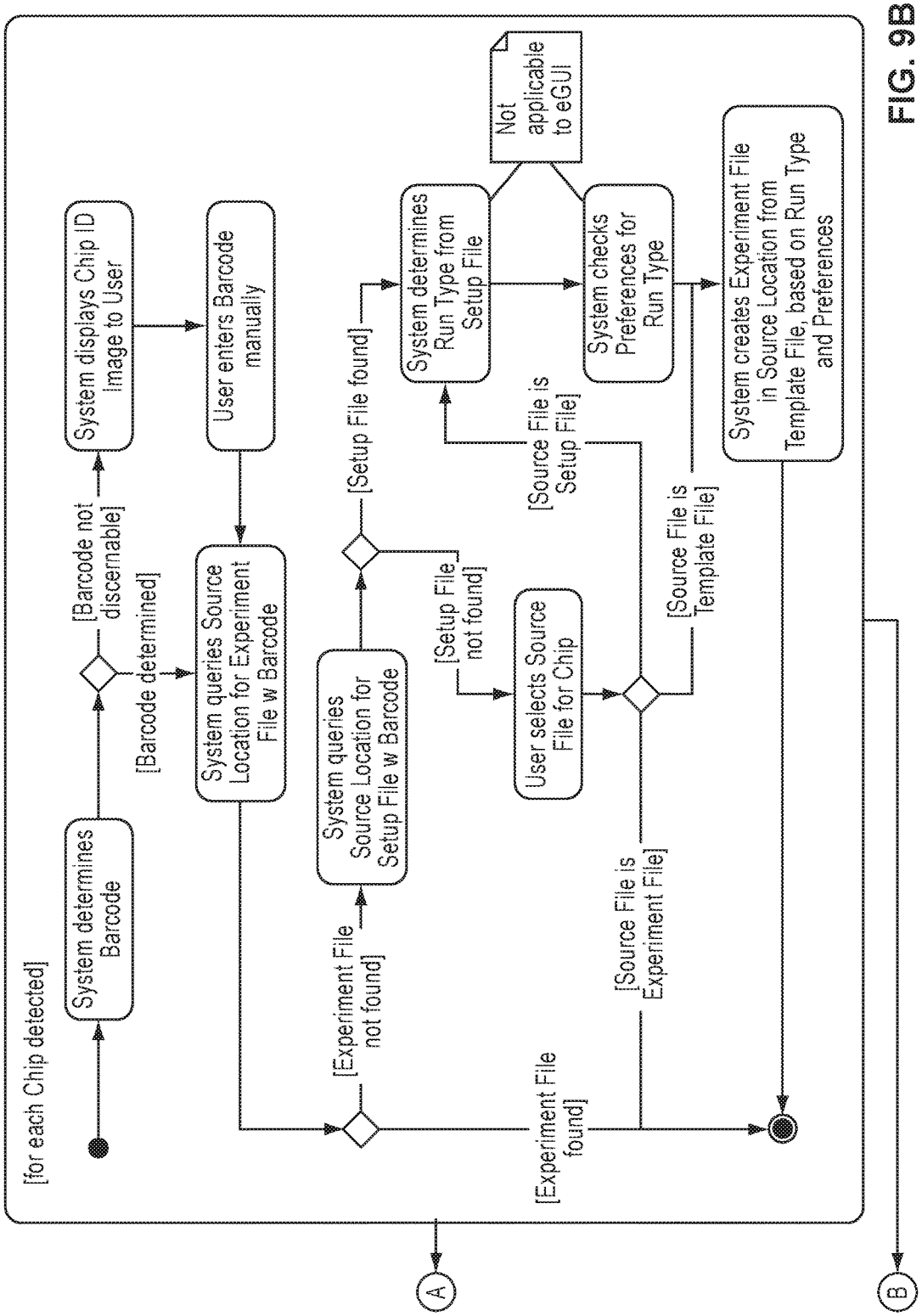

An exemplary workflow, based on reading two identifiers on an object of interest, is depicted in FIGS. 9A and 9B. Additionally, two examples of workflows, according to various embodiments are described as follows.

From client software (desktop) or instrument LCD panel:
1) User invokes Start Run operation.
2) System prompts user to enter Barcodes for substrates to be run.
3) User physically loads four substrates into instrument.
4) User invokes "Read Barcode" operation from software.
Option A—User launches Start OA Run workflow from Software:
Pre-Conditions:
  User loads up to four substrates into instrument
  User saves Experiment files, Template files or Setup files to default file location(s) in Software
1. Software creates substrate Run object 2. Instrument captures multiple CCD images of all substrates, which includes the barcode and alphanumeric code on each loaded chip
3. For each substrate image:
   a. Barcode region is derived and parses the image to determine the Barcode
   b. Alphanumeric code region is derived and parses the image to determine the alpha-numeric code
   c. Barcode and alpha-numeric code results are determined
   d. Barcode result is validated against alphanumeric code result
   e. An experiment file is retrieved from default file location for alphanumeric code
   f. If experiment file not found, run setup file retrieved from default file location for alphanumeric code
   g. If run setup file found, Uniquely Named Protocol from Run Setup file is determined and queries/retrieves associated Run Protocol
   h. User can manually browse/select alternative experiment file, run setup file or template file for the substrate
   i. User can manually browse/select a sample setup file for the substrate
   j. System derives experiment filename for substrate; user can manually change filename
4. Run Protocol is applied to the OA Run object
5. User invokes Start OA Run operation
6. Run Protocols and existing Experiment files for each loaded OA is validated based on compatibility
   a. Error handling condition
7. For each loaded substrate, Experiment file is created/updated with the following information:
   a. Run Protocol
   b. Assay assignments to Well Positions
   c. Sample assignments to Well Positions
8. Start OA Run command API is run
Option B—User launches Start substrate run workflow from LCD panel:
Pre-Conditions:
  User loads up to four substrates into instrument
  User saves experiment files or template files to default file location(s) in instrument
1. Firmware creates substrate Run object
2. Instrument captures multiple CCD images of all substrates, which includes the Barcode and Chip ID on each loaded chip
3. For each Chip Image:
   a. Barcode region is derived and parses the image to determine the Barcode
   b. Alphanumeric code region is derived and parses the image to determine the alpha-numeric code
   c. Barcode and alphanumeric code results are returned
   d. Barcode result is validated against alphanumeric code result
   e. Experiment file from default file location is retrieved for alphanumeric code
   f. User can manually browse/select alternative experiment file or template file for the substrate
   g. Experiment filename for substrate is derived; user can manually change filename
4. Run Protocol is derived for the substrate Run object
5. User invokes Start substrate Run operation
6. Run Protocols and existing experiment files for each loaded substrate are validated for compatibility
   a. Error handling condition 7. For each loaded substrate, experiment file with the following information is created/updated:
   a. Run Protocol
   b. Assay assignments to well positions
   c. Sample assignments to well positions
8. Firmware starts substrate run Therefore, according to the above, some examples of the disclosure comprise the following:

In one example, a computer-implemented method for identifying a first object-of-interest, wherein the first object-of-interest includes two identifiers and a sample portion, is provided. The method comprises: imaging the first object-of-interest including the two identifiers, wherein the imaging generates a first set of image data; determining a position of the first object-of-interest in the field-of-view of an optical sensor; determining the two identifiers from the first set of image data; and identifying the first object-of-interest based on the two identifiers.

Additionally or alternatively, in one or more of the examples disclosed above, the computer-implemented method of claim 1 further comprises: imaging a second object-of-interest, wherein the second object-of-interest includes two identifiers, wherein the imaging generates a second set of image data; determining a position of a second substrate in the field-of-view of the optical sensor, wherein the second substrate includes two identifiers and a sample portion; determining the two identifiers of the second substrate; and identifying the second substrate based on the two identifiers of the second object-of-interest.

Additionally or alternatively, in one or more of the examples disclosed above, the first and second object-of-interest is a first and second substrate.

Additionally or alternatively, in one or more of the examples disclosed above, the computer-implemented method, further comprises: determining compatibility of testing the first and second substrates in a same sample run.

Additionally or alternatively, in one or more of the examples disclosed above, one of the two identifiers is an alpha-numeric code.

Additionally or alternatively, in one or more of the examples disclosed above, one of the two identifiers is a barcode.

Additionally or alternatively, in one or more of the examples disclosed above, the identifying includes independent validation of the first substrate based on each of the two identifiers.

Additionally or alternatively, in one or more of the examples disclosed above, the positioning is based on at least one identifier being within a predetermined region of the field-of-view of the optical sensor.

In another example, a computer-readable storage medium encoded with instructions, executable by a processor, identifying a first object-of-interest, wherein the first object-of-interest includes two identifiers and a sample portion, is provided. The instructions comprising instructions for: imaging the first object-of-interest including the two identifiers, wherein the imaging generates a first set of image data; determining a position of the first object-of-interest in the field-of-view of an optical sensor; determining the two identifiers from the first set of image data; and identifying the first object-of-interest based on the two identifiers.

Additionally or alternatively, in one or more of the examples disclosed above, the instructions further include instructions for: imaging a second object-of-interest, wherein the second object-of-interest includes two identifiers, wherein the imaging generates a second set of image data; determining a position of a second substrate in the field-of-view of the optical sensor, wherein the second substrate includes two identifiers and a sample portion; determining the two identifiers of the second substrate; and identifying the second substrate based on the two identifiers of the second object-of-interest.

Additionally or alternatively, in one or more of the examples disclosed above, the first and second object-of-interest is a first and second substrate.

Additionally or alternatively, in one or more of the examples disclosed above, the computer-readable medium further comprises instructions for determining compatibility of testing the first and second substrates in a same sample run.

Additionally or alternatively, in one or more of the examples disclosed above, one of the two identifiers is an alpha-numeric code.

Additionally or alternatively, in one or more of the examples disclosed above, one of the two identifiers is a barcode.

Additionally or alternatively, in one or more of the examples disclosed above, the identifying includes independent validation of the first substrate based on each of the two identifiers.

Additionally or alternatively, in one or more of the examples disclosed above, the positioning is based on at least one identifier being within a predetermined region of the field-of-view of the optical sensor.

In another example, a system for identifying a first substrate, wherein the first substrate includes two identifiers and a sample portion, is provided. The system comprises: a processor; and a memory encoded with instructions, executable by the processor, the instructions for: imaging the first object-of-interest including the two identifiers, wherein the imaging generates a first set of image data; determining a position of the first object-of-interest in the field-of-view of an optical sensor; determining the two identifiers from the first set of image data; and identifying the first object-of-interest based on the two identifiers.

Additionally or alternatively, in one or more of the examples disclosed above, one of the two identifiers is an alpha-numeric code.

Additionally or alternatively, in one or more of the examples disclosed above, one of the two identifiers is a barcode.

Although the present invention has been described with respect to certain exemplary embodiments, examples, and applications, it will be apparent to those skilled in the art that various modifications and changes may be made without departing from the invention.

What is claimed is:

1. A computer-implemented method for identifying a first object-of-interest, wherein the first object-of-interest includes two identifiers and a sample portion, the method comprising:
   loading the first object-of-interest into an instrument for performing a biological analysis of biological components included in the sample portion;
   imaging the first object-of-interest including the two identifiers, wherein the imaging generates a first set of image data;
   determining a position of the first object-of-interest in a field-of-view of an optical sensor;
   determining the two identifiers from the first set of image data, wherein one of the two identifiers is a barcode;
   identifying the first object-of-interest based on the two identifiers; and selecting a type of biological analysis of biological components included in the sample portions on the first object-of-interest to perform by the instrument based on the identification of the two identifiers.

2. The computer-implemented method of claim 1, further comprising:
imaging a second object-of-interest, wherein the second object-of-interest includes two identifiers, wherein the imaging generates a second set of image data;
determining a position of a second object-of-interest in the field-of-view of the optical sensor, wherein the second object-of-interest includes two identifiers and a sample portion;
determining the two identifiers of the second object-of-interest; and
identifying the second object-of-interest based on the two identifiers of the second object-of-interest.

3. The computer-implemented method of claim 2, wherein the first and second object-of-interest is a first and second substrate.

4. The computer-implemented method of claim 2, further comprising:
determining compatibility of testing the first and second object-of-interests in a same sample run.

5. The computer-implemented method of claim 1, wherein one of the two identifiers is an alpha-numeric code.

6. The computer-implemented method of claim 1, wherein the identifying includes independent validation of the first object-of-interest based on each of the two identifiers.

7. The computer-implemented method of claim 1, wherein the positioning is based on at least one identifier being within a predetermined region of the field-of-view of the optical sensor.

8. A non-transitory computer-readable storage medium encoded with instructions, executable by a processor, identifying a first object-of-interest, wherein the first object-of-interest includes two identifiers and a sample portion, the instructions comprising instructions for:
determining the first object-of-interest is loaded into an instrument for performing a biological analysis of biological components included in the sample portion;
imaging the first object-of-interest including the two identifiers, wherein the imaging generates a first set of image data;
determining a position of the first object-of-interest in a field-of-view of an optical sensor;
determining the two identifiers from the first set of image data, wherein one of the two identifiers is a barcode;
identifying the first object-of-interest based on the two identifiers; and
selecting a type of biological analysis of biological components included in the sample portions on the first object-of-interest to perform by the instrument based on the identification of the two identifiers.

9. The non-transitory computer-readable storage medium of claim 8, wherein one of the two identifiers is an alpha-numeric code.

10. The non-transitory computer-readable storage medium of claim 8, wherein the identifying includes independent validation of the first object-of-interest based on each of the two identifiers.

11. The non-transitory computer-readable storage medium of claim 8, wherein the positioning is based on at least one identifier being within a predetermined region of the field-of-view of the optical sensor.

12. The non-transitory computer-readable storage medium of claim 8, wherein the instructions further include instructions for:
imaging a second object-of-interest, wherein the second object-of-interest includes two identifiers, wherein the imaging generates a second set of image data;
determining a position of a second substrate in the field-of-view of the optical sensor, wherein the second substrate includes two identifiers and a sample portion;
determining the two identifiers of the second substrate; and
identifying the second substrate based on the two identifiers of the second object-of-interest.

13. The non-transitory computer-readable storage medium of claim 12, wherein the first and second object-of-interest is a first and second substrate.

14. The non-transitory computer-readable storage medium of claim 12, further comprising:
determining compatibility of testing the first and second substrates in a same sample run.

15. A system for identifying a first substrate, wherein the first substrate includes two identifiers and a sample portion, the system comprising:
a processor; and
a memory encoded with instructions, executable by the processor, the instructions for:
determining a first object-of-interest is loaded into an instrument for performing a biological analysis of biological components included in the sample portion;
imaging the first object-of-interest including the two identifiers, wherein the imaging generates a first set of image data;
determining a position of the first object-of-interest in a field-of-view of an optical sensor;
determining the two identifiers from the first set of image data, wherein one of the two identifiers is a barcode;
identifying the first object-of-interest based on the two identifiers; and
selecting a type of biological analysis of biological components included in the sample portions on the first object-of-interest to perform by the instrument based on the identification of the two identifiers.

16. The system of claim 15, wherein one of the two identifiers is an alpha-numeric code.

* * * * *